US010603028B2

(12) United States Patent
Sengun et al.

(10) Patent No.: US 10,603,028 B2
(45) Date of Patent: Mar. 31, 2020

(54) FINGER TRAPS FOR COLLAPSIBLE SUTURE LOOPS

(71) Applicant: Medos International Sárl, Le Locle (CH)

(72) Inventors: Mehmet Z. Sengun, Canton, MA (US); David B. Spenciner, North Attleboro, MA (US); Richard M. Lunn, Kingston, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 119 days.

(21) Appl. No.: 15/622,360

(22) Filed: Jun. 14, 2017

(65) Prior Publication Data

US 2018/0360437 A1     Dec. 20, 2018

(51) Int. Cl.
*A61B 17/04* (2006.01)

(52) U.S. Cl.
CPC ...... *A61B 17/0401* (2013.01); *A61B 17/0485* (2013.01); *A61B 17/0487* (2013.01); *A61B 2017/0409* (2013.01); *A61B 2017/0464* (2013.01); *A61B 2017/0475* (2013.01); *A61B 2017/0477* (2013.01)

(58) Field of Classification Search
CPC ............ A61B 17/0401; A61B 17/0487; A61B 17/0466; A61B 2017/0403–0408; A61B 2017/0412–0414; A61B 2017/0417–0464; A61B 2017/06185; A61F 2/08–2002/0894
See application file for complete search history.

(56) References Cited

U.S. PATENT DOCUMENTS

| 7,601,165 | B2 | 10/2009 | Stone |
| 7,658,751 | B2 | 2/2010 | Stone et al. |
| 7,857,830 | B2 | 12/2010 | Stone et al. |
| 7,905,904 | B2 | 3/2011 | Stone et al. |
| 7,909,851 | B2 | 3/2011 | Stone et al. |
| 7,959,650 | B2 | 6/2011 | Kaiser et al. |
| 8,137,382 | B2 | 3/2012 | Denham et al. |
| 8,292,921 | B2 | 10/2012 | Stone et al. |

(Continued)

FOREIGN PATENT DOCUMENTS

| EP | 2277455 A2 | 1/2011 |
| WO | WO-2014117107 A1 | 7/2014 |
| WO | WO-2014146023 A2 | 9/2014 |

OTHER PUBLICATIONS

U.S. Appl. No. 15/297,696 entitiled "Meniscal Repair Devices, Systems, and Methods" filed Oct. 19, 2016.

(Continued)

*Primary Examiner* — Katrina M Stransky
*Assistant Examiner* — Brigid K Byrd

(57) ABSTRACT

Finger traps for collapsible suture loops are provided. In general, a suture coupled to an implant can be tensioned to facilitate desirable positioning of the implant relative to tissue in a patient's body. The suture can include a finger trap and a knot. In general, the finger trap is a hollow area of the suture through which the suture passes through itself and is configured to slide in a single direction when under tension. In an exemplary embodiment, the knot is located along a length of the suture that is closer than the finger trap to a tail of the suture that is being pulled to tension the suture.

18 Claims, 4 Drawing Sheets

(56) References Cited

U.S. PATENT DOCUMENTS

| | | |
|---|---|---|
| 8,366,744 B2 | 2/2013 | Bojarski et al. |
| 8,562,647 B2 | 10/2013 | Kaiser et al. |
| 8,790,369 B2 | 7/2014 | Orphanos et al. |
| 8,814,903 B2 | 8/2014 | Sengun et al. |
| 9,107,653 B2 | 8/2015 | Sullivan |
| 9,173,645 B2 | 11/2015 | Overes et al. |
| 9,179,950 B2 | 11/2015 | Zajac et al. |
| 9,345,471 B2 | 5/2016 | Sullivan |
| 9,463,011 B2 | 10/2016 | Dreyfuss et al. |
| 2005/0033363 A1* | 2/2005 | Bojarski ............ A61B 17/0401 606/228 |
| 2012/0016386 A1* | 1/2012 | Bojarski ............ A61B 17/0401 606/148 |
| 2012/0290006 A1 | 11/2012 | Collins et al. |
| 2013/0023928 A1* | 1/2013 | Dreyfuss ............ A61B 17/0401 606/228 |
| 2015/0032157 A1 | 1/2015 | Dooney, Jr. et al. |
| 2015/0201929 A1 | 7/2015 | Dooney, Jr. et al. |
| 2016/0235396 A1 | 8/2016 | Sullivan |

OTHER PUBLICATIONS

Extended European Search Report for EP App. No. 18177826.7 dated Nov. 15, 2018 (7 pages).

\* cited by examiner

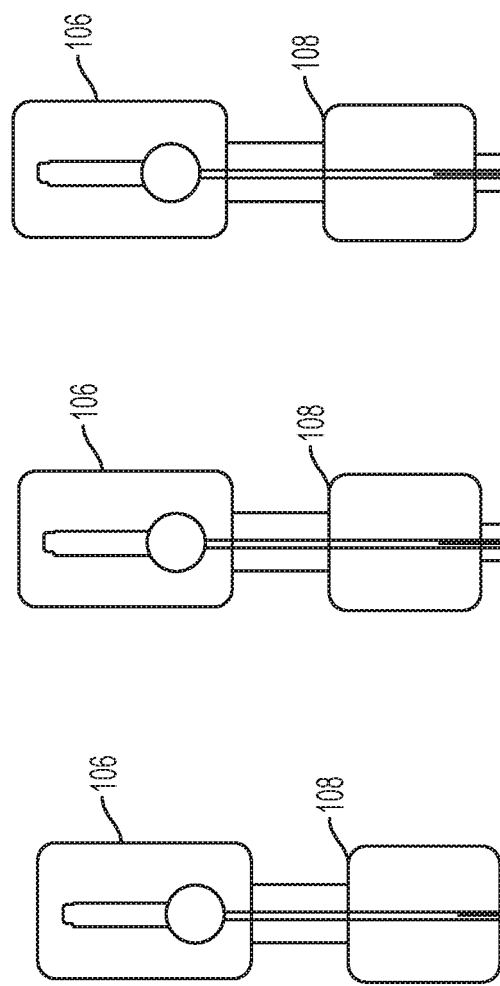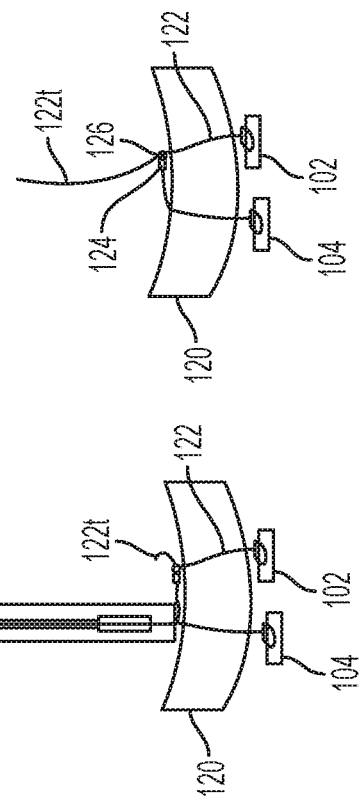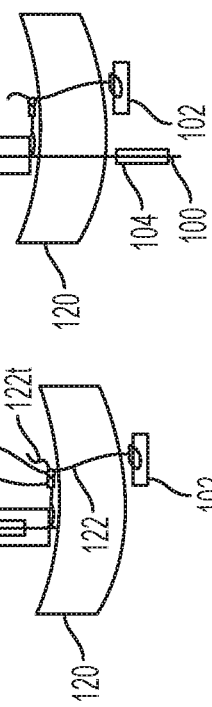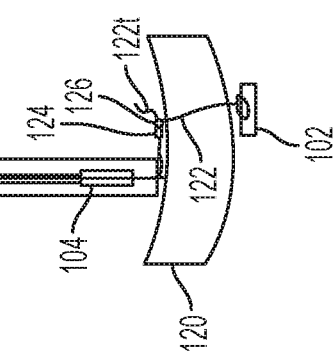

US 10,603,028 B2

FINGER TRAPS FOR COLLAPSIBLE SUTURE LOOPS

FIELD

The present disclosure relates generally to finger traps for collapsible suture loops.

BACKGROUND

A variety of injuries and conditions require repair of soft tissue damage, or reattachment of soft tissue to bone and/or surrounding tissue. For example, when otherwise healthy tissue has been torn away from a bone, such as a shoulder rotator cuff tendon being partially or completely torn from a humerus (a rotator cuff tear), surgery is often required to reattach the tissue to the bone, to allow healing and a natural reattachment to occur. A number of devices and methods have been developed for performing these surgical repairs. Some of the more successful methods including the use of suture fixation members, such as suture anchors, which typically include an anchor body having one or more suture attachment feature and include a tissue or bone engaging feature for retaining the suture anchor within or adjacent to the tissue or bone. Depending on the specific injury, one or more suture anchors connected to, or interconnected by, one or more segment of suture, may be used to perform the repair.

Surgery can also be required when a tear occurs in the substance of a single type of tissue, for example in the meniscus of the knee (a meniscal tear). One method of repairing such a tear is to stitch it closed by passing a length of suture through the tissue and tying the suture. Suture can also be used in conjunction with one or more suture anchors to repair such tissue tears. Sutures can be fastened to suture anchors and to tissue using knots tied by the surgeon during a repair procedure, or using "knotless" devices and methods, where one or more anchors and one or more sutures can be connected and tensioned without the surgeon needing to tie knots during the surgery. Knotless anchoring is of particular utility for minimally invasive surgeries, such as endoscopic or arthroscopic repairs, where the surgeon remotely manipulates the suture at the surgical site using tools inserted through a small diameter cannula or endoscopic tube, which can make the knotting process difficult and tedious.

Additionally, it can be difficult to deliver and position the anchors at a desired angle and location relative to the tissue, such as by the anchors moving from an intended location and angular orientation because of the suture attached thereto being knotted, pulled, and/or tensioned during the surgery. Anchors not being desirably angled and located may result in anchors positioned at a compromised angle and location instead of a more desirable angle and location and/or may result in one or more failed attempts at anchor delivery before desired angle and location is achieved.

Accordingly, there remains a need for improved tissue repair devices, systems, and methods.

SUMMARY

In general, finger traps for collapsible suture loops are provided.

In one aspect, a surgical device is provided that in one embodiment includes a first implantable anchor, a second implantable anchor, and a suture coupled to the first and second anchors. The suture has a first length extending from the first anchor toward the second anchor and has a second length extending from the second anchor toward the first anchor, the first length has a knot formed therein, and the second length passes through an interior collapsible passage formed in the first length and then passes through the knot with a tail of the suture extending from the knot.

The surgical device can have any number of variations. For example, the knot can be an overhand knot.

For another example, the tail of the suture can be configured to be pulled in a first direction toward the first anchor to tension the suture, and can be configured to be pulled in a second, different direction to tension the suture. In at least some embodiments, pulling the tail of the suture in the first direction can be configured to reduce a distance between the first and second anchors, and pulling the tail of the suture in the second direction can be configured to reduce the distance between the first and second anchors. In at least some embodiments, pulling the tail of the suture in the first direction can be configured to cause the suture to slide within the interior passage and through the knot, and pulling the tail of the suture in the second direction can be configured to cause the suture to slide within the interior passage and through the knot. In at least some embodiments, the suture can be slidable through the interior passage in only the first direction.

For yet another example, the second length can exit the interior passage before passing through the knot. For still another example, the first anchor can have a first hole through which the suture extends, and the second anchor can have a second hole through which the suture extends. For another example, the surgical device can include a second suture coupled to the second anchor and having the first suture looped therethrough so as to couple the suture to the second anchor. For still another example, the suture can be braided from a plurality of threads.

In another embodiment, a surgical device includes a first implantable anchor, a second implantable anchor, and a suture slidably coupled to the first and second anchors. The suture has a collapsible hollow portion through which another portion of the suture passes through, the suture has a knot formed therein adjacent to the hollow portion such that a tail of the suture passes through the hollow portion and then passes through the knot, and the tail is configured to be pulled to slide the suture through the hollow portion and through the knot.

The surgical device can vary in any number of ways. For example, the knot can be an overhand knot. For another example, the tail can be configured to be pulled in any direction to slide the suture through the hollow portion and through the knot. For yet another example, the hollow portion and the knot can be located along a length of suture extending between the first and second anchors. For still another example, pulling the tail to slide the suture through the hollow portion and through the knot can reduce a distance between the first and second anchors.

In another aspect, a surgical method is provided that includes advancing a suture, a first anchor, and a second anchor into a body of a patient with the suture extending between the first and second anchors, having a knot formed therein, and having a hollow portion adjacent the knot through which another portion of the suture extends. The surgical method also includes positioning the first and second anchors adjacent a tissue and then tensioning the suture to cause the suture to slide through the knot and through the hollow portion and cause the first and second anchors to move relative to the tissue.

The surgical method can vary in any number of ways. For example, the suture can be uni-directionally slidable through the hollow portion in a first direction, and tensioning the suture can include pulling a tail of the suture extending from the knot in the first direction. For another example, the suture can be uni-directionally slidable through the hollow portion in a first direction, and tensioning the suture can include pulling a tail of the suture extending from the knot in a second, different direction. For yet another example, the tissue can be at one of a knee, a hip, and a shoulder of the patient.

BRIEF DESCRIPTION OF DRAWINGS

This invention will be more fully understood from the following detailed description taken in conjunction with the accompanying drawings, in which:

FIG. 14 is a side schematic view of the tissue of FIG. 13 with the delivery system changed in position relative thereto;

FIG. 15 is a side schematic view of the tissue of FIG. 14 with the needle and the other of the implants advanced therethrough;

FIG. 16 is a side schematic view of the tissue of FIG. 15 with the needle withdrawn; and FIG. 17 is a side schematic view of the tissue of FIG. 16 with the delivery system removed.

DETAILED DESCRIPTION

Figure 1:
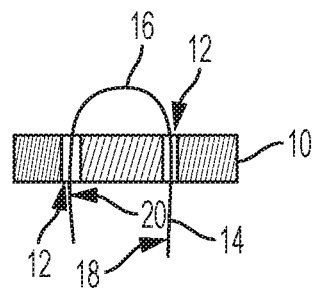
FIG. 1 is a side cross-sectional schematic view of one embodiment of an implant having a suture coupled thereto.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Finger traps for collapsible suture loops are provided. In general, a suture coupled to an implant can be tensioned to facilitate desirable positioning of the implant relative to tissue in a patient's body. The suture can include a finger trap and a knot. In general, the finger trap is a hollow area of the suture through which the suture passes through itself and is configured to slide in a single direction when under tension. In an exemplary embodiment, the knot is located along a length of the suture that is closer than the finger trap to a tail of the suture that is being pulled to tension the suture. In this way, the knot can help guide the suture to slide through the finger trap in the single direction through which the suture is configured to freely slide through the finger trap regardless of the direction in which the suture tail is being pulled. The suture may thus be less likely to be damaged since it is prevented from sliding through the finger trap in a direction other than the single direction, and/or tensioning may be accomplished faster and/or easier since the suture tail can be pulled in any direction to tension the suture without a surgeon or other user first determining which is the single direction in which the suture should be pulled to properly slide through the finger trap.

In general, the implants discussed herein, also referred to herein as anchors, are configured to be implanted in a body of a patient. The implants are configured to couple to a suture and to be used in a tissue repair procedure, e.g., an arthroplasty at a joint such as the hip, knee, or shoulder, a meniscal repair procedure for repairing a meniscal tear at a knee, a rotator cuff repair procedure for repairing a torn rotator cuff at a shoulder, etc.

An implant can be absorbable or non-absorbable. An implant can be made from any of a variety of materials, e.g., Polyether ether ketone (PEEK), Polylactic acid or polylactide (PLA), BIOCRYL® RAPIDE®, stainless steel, etc. An implant can be formed by a variety of techniques, for example by an injection molding process such as overmolding or by a post-molding process such as post-molding machining. An implant can have any of a variety of sizes as appropriate for, e.g., use at a particular anatomical location and with a particular patient.

FIG. 1 illustrates one embodiment of an implant 10 configured to be implanted in a body of a patient to facilitate tissue repair. The implant 10 has an elongate, rectangular shape in this illustrated embodiment, but the implant 10 can have other shapes. The implant 10 has at least one passageway 12 formed therethrough that is configured to receive a suture 14 therethrough. In this illustrated embodiment, the implant 10 has two passageways 12. Having a plurality of passageways 12 allows the suture 14 to be looped through the implant 10 as shown, for example, in FIG. 1 with the suture 14 passing in one direction through one of the passageways 12 and in an opposite direction through the other passageway 12 with a length 16 of the suture 14 extending between the passageways 12 on one side of the implant 10 and first and second tails 18, 20 of the suture 14 extending from the other side of the implant 10. The suture 14 in this illustrated embodiment is a single suture 14, but the implant 10 and other implants discussed herein can be coupled to multiple sutures, e.g., with multiple sutures passing through the implant's at least one passageway.

The suture 14 can be any type of suture and can be made from any of a variety of materials, including natural materials and synthetic materials. Examples of materials for the suture 14 include polymers, such as polyglycolide, polypropylene, polyethylene terephthalate (PET), and polydioxanone, and fabrics, such as nylon and silk. The suture 14 can be bioabsorbable, partially bioabsorbable, or nonabsorbable, and can have a circular cross section or another cross section. In one embodiment, the suture 14 is partially bioabsorbable, comprising polyethylene as a nonabsorbable component, and polydioxanone as a bioabsorbable component.

The suture 14 can be formed from a single thread or from a plurality of threads. The plurality of threads can be coupled together to define a suture strand in any of a variety of ways, such as by being braided together. In an exemplary embodiment, the thread(s) that form the suture 14 are flexible to allow the suture 14 to be flexible, as in the illustrated embodiment. The threads that form the suture 14 can made from different materials, e.g., a first number of the threads being nylon and a second number of the threads being PET, or can all be made from the same material. A suture 14 formed from a plurality of threads can, in some embodiments, include a core around which the threads are arranged, such as by braiding. The core may provide the suture 14 with strength to help prevent the suture 14 from breaking, snapping, etc. The suture 14 can have any of a variety of sizes, such as a size in a range of about size #5 to #5-0.

Figure 2:
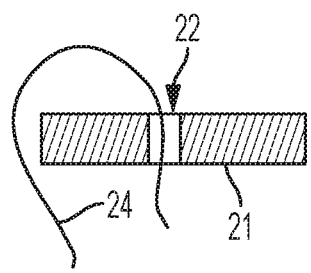
FIG. 2 is a side cross-sectional schematic view of another embodiment of an implant having a suture coupled thereto.

FIG. 2 shows another embodiment of an implant 21 that includes at least one passageway 22 therethrough, which is a single passageway 22 in this illustrated embodiment. FIG. 2 also shows a suture 24 extending through the passageway 22 by being looped therethrough to couple the suture 24 to the implant 21.

Figure 3:
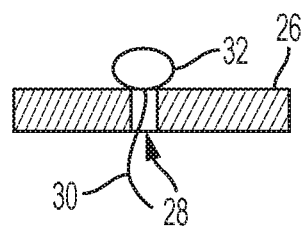
FIG. 3 is a side cross-sectional schematic view of yet another embodiment of an implant having a suture coupled thereto.

FIG. 3 shows another embodiment of an implant 26 that includes at least one passageway 28 therethrough, which is a single passageway 28 in this illustrated embodiment. FIG. 3 also shows a suture 30 extending through the passageway 28. The suture 30 has a knot 32 therein with a diameter greater than a diameter of the passageway 28 such that the knot 32 cannot be pulled or otherwise moved through the passageway 28, thereby helping the suture 30 remain coupled to the implant 26. In an embodiment in which an implant has a plurality of passageways, each of the passageways can have an associated suture extending therethrough with a knot therein.

Figure 4:
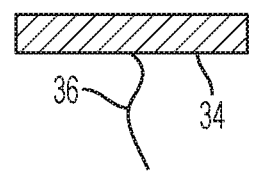
FIG. 4 is a side cross-sectional schematic view of still another embodiment of an implant having a suture coupled thereto.

FIG. 4 shows another embodiment of an implant 34 having a single suture 36 coupled thereto. The suture 36 in this illustrated embodiment is coupled to the implant 34 by having an end (or other portion) thereof attached thereto, such as by crimping, adhesion with an adhesive, being tied around the implant 34, etc. If the implant 34 is coupled to a plurality of sutures, each of the sutures can be attached to the implant 36 in the same way (e.g., each attached thereto with adhesive, each tied around the implant, etc.) or in different ways (e.g., one suture adhered thereto with adhesive and another attached thereto by being tied therearound, etc.).

Exemplary embodiments of implants are further described in U.S. patent application Ser. No. 15/297,696 entitled "Meniscal Repair Devices, Systems, and Methods" filed Oct. 19, 2016, which is hereby incorporated by reference in its entirety.

Following delivery of an implant into a body of a patient, the suture(s) attached to the implant are tensioned to secure the implant in position relative to a target, e.g., a target tissue being repaired. The suture(s) being able to slide relative to the implant after the delivery of the implant into the patient's body facilitates the tensioning of the suture(s) and hence facilitates secure positioning of the implant within the patient's body to aid in proper healing.

Figure 5:
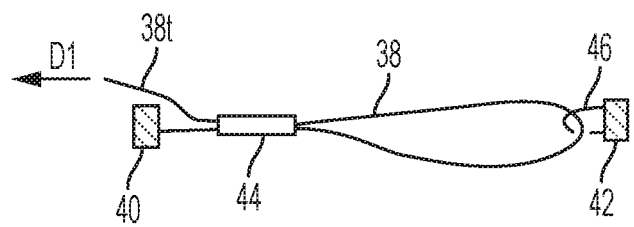
FIG. 5 is a schematic view of one embodiment of a suture with a finger trap, the suture coupled to first and second anchors and being pulled in a first direction.
Figure 6:
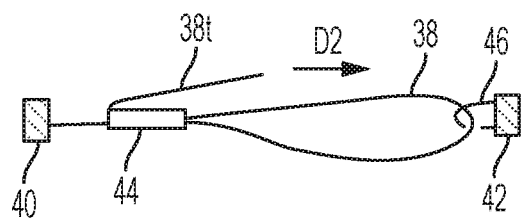
FIG. 6 is a schematic view of the suture and first and second anchors of FIG. 5 with the suture being pulled in a second, opposite direction.

FIGS. 5 and 6 illustrate one technique for attaching a suture 38 to first and second implants 40, 42 using a finger trap 44. The finger trap 44 is an area of the suture 38 that is hollow and through which the suture 38 passes through itself, and when under tension is slidable uni-directionally in a first direction D1, and is locked from sliding in the other, opposite direction D2. The first implant 40 is coupled directly to the suture 38, and the second implant 42 is coupled indirectly to the suture 38 with a second suture 46 that is looped through the suture 38. After the implants 40, 42 are positioned relative to a target tissue in a patient's body, the suture 38 can be tensioned by pulling on a tail 38t of the suture 38 in the first direction D1, as shown in FIG. 5, which slides the suture 38 through the finger trap 44. In some instances, the suture tail 38t may be tensioned by pulling thereon in the second direction D2 and/or in another direction other than the first direction D1 due to any number of factors such as space constraints at the surgical site, obscured visualization of the surgical site, a surgeon's angle of approach to the surgical site, etc. However, if the suture tail 38t is pulled in the second direction D2 and/or other direction other than the first direction D1 to tension the suture 38, the suture 38 experiences stress that can cause any of one or more problems. For example, the suture 38 can break entirely such that the suture 38 cannot secure the implants 40, 42 to the target tissue. For another example, individual threads forming the suture 38 can break without the entire suture 38 breaking, which may lead to complete breakage of the suture 38 at some future time and/or may result in one or both of the implants 40, 42 not being properly positioned due to partial suture 38 failure. For yet another example, braided threads forming the suture 38 may become less tightly braided, which may result in decreasing the functional length of the finger trap 44 and in turn result in one or both of the implants 40, 42 not being properly positioned due to the suture 38 being loosened. For still another example, the hollow suture area at the finger trap 44 can expand in diameter due to pulling in a direction other than the first direction D1, which may weaken the suture 38 at or near the finger trap 44 so as to increase the chance of future suture 38 breakage.

Figure 7:
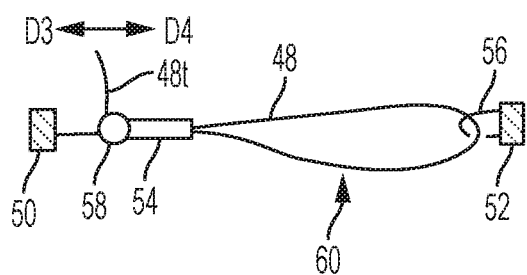
FIG. 7 is a schematic view of another embodiment of a suture with a finger trap, the suture coupled to first and second anchors.

FIG. 7 illustrates another technique for attaching a suture 48 to first and second implants 50, 52 using a finger trap 54. The first implant 50 is coupled directly to the suture 48, e.g., via a technique such as any of the techniques of FIGS. 1-4, and the second implant 52 is coupled indirectly to the suture 48 with a second suture 56 that is looped through the suture 48. In other embodiments, the first and second implants 50, 52 can be coupled to the suture 48 in other ways, e.g., both of the implants 50, 52 being directly coupled to the suture 48, both of the implants 50, 52 being indirectly coupled to the suture 48, or the first implant 50 being indirectly coupled to the suture 48 and the second implant 52 being directly coupled to the suture 48. Also, a single suture 48 is coupled to the implants 50, 52 in this illustrated embodiment, but as mentioned above, multiple sutures can be used.

The finger trap 54 is an area of the suture 48 that is hollow and through which the suture 48 passes through itself. The suture 48 in this illustrated embodiment when under tension is slidable uni-directionally in a first direction D3 through the finger trap 54 and is locked from sliding through the finger trap 54 in the other, opposite direction D4 because the tension collapses the finger trap 44 on the portion of the suture 48 passing therethrough. The suture 48 has a free end or tail 48t that extends from the finger trap 54.

The suture 48 in this illustrated embodiment has a knot 58 formed therein. The knot 58 is located adjacent to the finger trap 54, as shown in FIG. 7, and is located on a side of the finger trap 54 from which the suture tail 48t extends. The knot 58 substantially abuts the finger trap 54 when adjacent thereto. A person skilled in the art will appreciate that although a small distance may exist between the knot 58 and the finger trap 54 such that the knot 58 does not abut the finger trap 54 so as to be in direct contact with the finger trap 54, the knot 58 can nevertheless be considered to substantially abut the finger trap 54 due to any number of factors, such as manufacturing tolerance. As shown in FIG. 7, the suture 48 has a first length extending from the first implant 50 toward the second anchor 52. The first length of the suture 48 has the knot 58 and finger trap 54 formed therein, with the knot 58 being closer to the first anchor 50 than the finger trap 54 along the first length of the suture 48 and with the finger trap 54 being closer to the second anchor 52 than the knot 58 along the first length. The suture 48 also has a second length extending from the second implant 52 toward the first anchor 50 that passes through the finger trap 54, e.g., passes through the hollow area of the suture 48, and then passes through the knot 58 with the suture tail 48t extending from the knot 58. The suture 48 also defines an adjustable loop 60 that includes partial portions of each of the suture's first and second lengths.

A partial portion of the first length of the suture 48 extends between the knot 58 and the first anchor 50. This partial length of the suture 48 allows the suture 48 to extend through tissue with the first implant 50 on one side of the tissue and the knot 58 to be on or near the other side of the tissue, as discussed further below.

The suture 48 can be tensioned by pulling on the suture tail 48t to slide the suture 48 through the finger trap 54. The suture 48 sliding through the finger trap 54 collapses the adjustable loop 60 and reduces a distance between the first and second anchors 50, 52. This tensioning may occur after the implants 50, 52 are positioned relative to a target tissue in a patient's body to desirably position the implants 50, 52 relative to the tissue, as discussed herein. The suture tail 48t may in some instances be pulled in the first direction D3, the first in which the suture 48 is configured to bi-directionally slide through the finger trap 54. Pulling the suture 48 in the direction D3 of its uni-directional sliding will generally result in desirable movement and tensioning of the suture 48 without causing any damage to the suture 48. In some instances, as mentioned above, the suture 48 may be tensioned by pulling on the suture tail 48t in the second direction D4 and/or in another direction other than the first direction D3 due to any number of factors. The knot 58 in the suture 48 is configured to reduce stress on the suture 48 and the finger trap 54 thereof when pulled through the finger trap 54 in a direction other than the first direction D3, thereby reducing chances of the suture 48 and the finger trap 54 thereof being damaged during the pulling of the suture tail 48t. The suture 48 and the finger trap 54 of FIG. 7 is thus less likely to be damaged than the suture 38 and the finger trap 44 of FIGS. 5 and 6 which does not have a knot formed therein, and is easier to use than the suture 38 of FIGS. 5 and 6 since the suture 48 of FIG. 7 can be pulled in any direction with minimal, if any, risk of damaging the suture 48 and the finger trap 54 thereof as the suture 48 slides through the finger trap 54. In general, the knot 58 is configured to reduce stress on the suture 48 when pulled through the finger trap 54 by acting like a pulley. In response to the suture tail 48t being pulled, the suture 48 will first be pulled at the knot 58 and then at the finger trap 54. In this way, the suture 48 may be directed through the finger trap 54 in the first direction D3 regardless of the direction in which the suture tail 48t is pulled. In other words, the knot 58 is configured to direct movement of the suture 48 through the finger trap 54 in the first direction D3, e.g., the suture's direction of uni-directional sliding. The knot's location along the suture 48 between the suture's free end 48t and the finger trap 54 facilitates this direction of suture movement through the finger trap 54. The knot 58 is also configured to provide cinching force to the suture 48 in addition to cinching force already provided by the finger trip 54, which may help hold the suture 48 in position post-tensioning.

Figure 8:
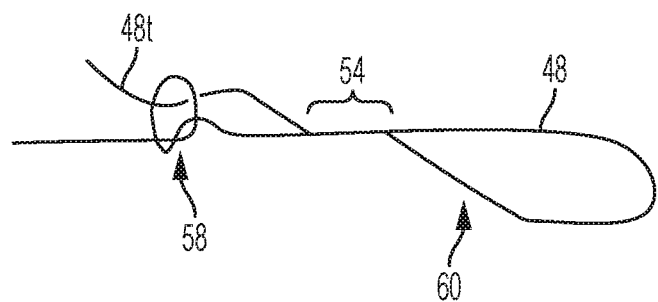
FIG. 8 is a schematic view of the suture of FIG. 7.

FIG. 8 illustrates one embodiment of forming the construct of the suture 48 as shown in FIG. 7. In this illustrated embodiment, the knot 58 is an overhand knot with the suture tail 48t passing through the knot 58. In general, the overhand knot is a knot in which the free end 48t of the suture 48 is tied around itself. The suture 48 is thus tied around itself at a location between the finger trap 54 and the first anchor 50. The overhand knot may be beneficial in surgical procedures due to its low profile, however, the knot 58 can have forms other than an overhand knot, such as a hitch knot or a bend knot. The knot 58 can be static (e.g., overhand half hitch), sliding (e.g., Duncan Loop), collapsing (e.g., cow hitch), etc.

The suture 48 in the illustrated embodiment of FIGS. 7 and 8 includes a single knot 58. In other embodiments, the suture 48 can include a plurality of knots 58 that form a stack or row of knots with a first knot 58 adjacent to the finger trap 54 similar to the knot 58 of FIG. 7 and with each of the one or more additional knots 58 being adjacent to the knot(s) on either side thereof along the suture's length.

The knot 58 in the illustrated embodiment of FIGS. 7 and 8 is formed by the suture 48 itself. In other embodiments, another suture can be attached to the suture 48 to form the knot 58, e.g., tied around the suture 48 to form the knot 58 thereon.

The implants coupled to at least one suture as described herein can be advanced through tissue in any of a variety of ways. For example, the implants and suture(s) can be delivered to a surgical site using one or more needles. The one or more needles can be configured to cut tissue (e.g., meniscus) to facilitate passage of the implant(s) associated therewith through the tissue since the implants may not be configured to cut tissue. An implant not being configured to cut tissue (e.g., the implant lacks a cutting surface) may help reduce chances of the implant inadvertently damaging tissue and/or other matter within the patient's body post-surgery.

In some embodiments, each of a plurality of implants coupled together with one or more sutures can be coupled to its own needle configured to advance its associated implant through tissue (e.g., meniscus in a meniscal repair procedure, rotator cuff tissue in a rotator cuff repair procedure, etc.) such that multiple needles are used to advance the implants through the tissue. Using multiple needles may require multiple incisions to be made in the patient, one incision for each needle, and may require an additional incision to facilitate the tying together of sutures threaded through tissue with the needles. In a meniscus repair procedure, for example, needles may be inserted through the sides of the knee instead of through the back of the knee in order to avoid possible damage to vital structures including veins and nerves at the back of the knee. In meniscus repair, use of multiple needles is generally referred to as an inside-out surgical technique. Exemplary embodiments of needles and use of multiple needles to deliver implants and sutures are further described in previously mentioned U.S. patent application Ser. No. 15/297,696 entitled "Meniscal Repair Devices, Systems, and Methods" filed Oct. 19, 2016.

In other embodiments, instead of using a plurality of needles to deliver a plurality of implants, each of a plurality of implants coupled together with one or more sutures can be coupled to a single needle configured to sequentially advance each of the implants through tissue (e.g., meniscus in a meniscal repair procedure, rotator cuff tissue in a rotator cuff repair procedure, etc.) such that only one needle is used to advance the implants through the tissue. Using a single needle may require only one incision to be made in the patient, which may provide any number of benefits over using multiple needles, such as improved cosmesis and less tissue trauma. In meniscus repair, use of a single needle is generally referred to as an all-inside surgical technique. Exemplary embodiments of single needles that can be used to deliver implants and sutures are further described in previously mentioned U.S. patent application Ser. No. 15/297,696 entitled "Meniscal Repair Devices, Systems, and Methods" filed Oct. 19, 2016.

A needle configured to deliver multiple implants can have a variety of sizes, shapes, and configurations. The needle can be made from any of a variety of materials, e.g., stainless steel, nitinol, etc. In an exemplary embodiment, the needle is a solid member and is flexible. The needle being solid may help provide structural stability to the needle. The needle being flexible may facilitate desired positioning of the needle relative to tissue through which it is desired to be advanced and/or may compensate for an angle of approach to the desired tissue not being ideal because the needle can be directed to tissue at another angle due to its flexibility. The needle, while flexible so as to allow flexing thereof has sufficient structural stability along its longitudinal length due to being solid and/or due to the material(s) from which the needle is made to allow the needle to be advanced longitudinally through tissue to deliver implant(s) therethrough. The needle can have a variety of sizes. In an exemplary embodiment, the needle has a maximum outer diameter of in a range of about 0.015 in. to 0.080 in., e.g., about 0.035 in. A distal tip of the needle can have a variety of configurations. In an exemplary embodiment, the distal tip of the needle can be sharp and configured to pierce through tissue, such as by being beveled or having a sharp triangular tip similar to a trocar tip. The needle having a sharp distal tip may facilitate penetration of the needle through tissue (e.g., meniscus, rotator cuff, etc.).

Figure 9:
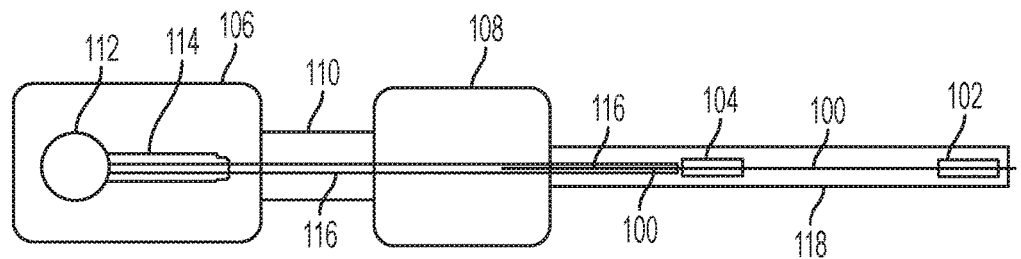
FIG. 9 is a partially transparent side schematic view of one embodiment of a delivery system having two implants disposed in a shaft thereof.

FIG. 9 illustrates one embodiment of a needle 100 configured to deliver a plurality of implants 102, 104 coupled to a suture 122 (obscured in FIG. 9) having a finger trap 124 and a knot 126 formed therein, such as the suture 48 of FIG. 7. The implants 102, 104 and the suture 122 can each have any of a variety of configurations, as discussed above. As also discussed above, the implants 102, 104 can each be coupled to the suture 122 in any of a variety of ways. The needle 100 in this illustrated embodiment is flexible and has a sharp distal tip. FIG. 9 shows the needle 100 as part of a delivery system configured to deliver the implants 102, 104. The delivery system includes a movable handle 106, a stationary handle 108, a spacer 110 along which the movable handle 106 is configured to selectively slide proximally and distally, an actuator 112 in the form of a knob selectively slidable proximally and distally in a slot 114 formed in the movable handle 106, a flexible tube 116 extending distally from the movable handle 106 and configured to slide in response to sliding movement of the actuator 112, and an elongate shaft 118 extending distally from the stationary handle 108.

FIG. 9 also shows first and second implants 102, 104 coupled to the needle 100. The first implant 102 is loaded on the needle 100 distal to the second implant 104 and is configured to be deployed from the needle 100 before the second implant 104 is deployed therefrom. The first and second implants 102, 104 are each cannulated to allow the needle 100 to pass therethrough. A proximal end surface of the second implant 104 abuts a distal end surface of the tube 116.

Figures 10, 11, 12, 13:
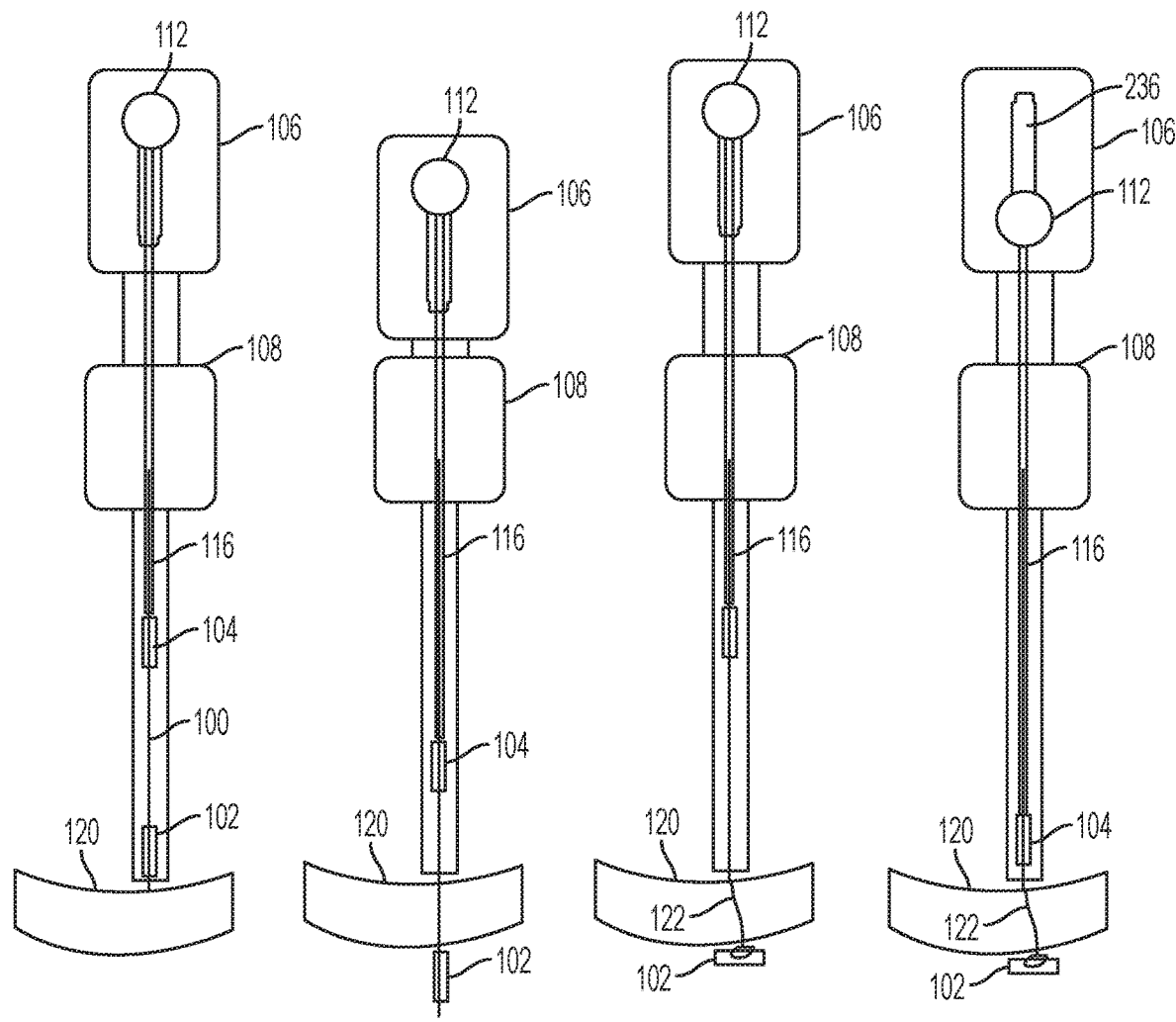
FIG. 10 is a side schematic view of tissue with the delivery system of FIG. 9 positioned adjacent thereto.
FIG. 11 is a side schematic view of the tissue of FIG. 10 with one of the implants advanced therethrough and with a needle of the delivery system advanced therethrough.
FIG. 12 is a side schematic view of the tissue of FIG. 11 with the needle withdrawn.
FIG. 13 is a side schematic view of the tissue of FIG. 12 with the other of the implants advanced within the shaft.

FIG. 10-17 illustrate one embodiment of use of the delivery system of FIG. 9 to deliver the implants 102, 104 loaded thereon. FIG. 10 shows the delivery system with a distal end thereof (e.g., a distal end of the elongate shaft 118) positioned adjacent tissue 120. A distal end of the needle 100 can extend distally beyond the distal end of the shaft 118, as shown in FIGS. 9 and 10, or the distal end of the needle 100 can be contained within an inner lumen of the elongate shaft 118 in which the needle 100 is slidably disposed.

FIG. 11 shows the needle 100 advanced through the tissue 120 with a distal tip of the needle 100 on a far side of the tissue 120, the first implant 102 also on the far side of the tissue 120, and the second implant 104 on a near side of the tissue 120 and still contained within the inner lumen of the elongate shaft 118 and having been pushed forward to keep its distance to the first implant 102. The needle 100 and the first implant 102 have been advanced through the tissue 120 by moving the movable handle 106 distally toward and relative to the stationary handle 108.

FIG. 12 shows the needle 100 retracted from the far side of the tissue 120 to the near side of the tissue 120 with the first implant 102 remaining on the far side of the tissue 120. The needle 100 has been retracted back through the tissue 120 by moving the movable handle 106 proximally away from and relative to the stationary handle 108.

FIG. 13 shows the second implant 104 having been advanced distally along the needle 100 by sliding the knob 112 distally in the slot 114 to slide the tube 116 distally and thereby push the second implant 104 distally. The tube 116 is now locked to the movable handle 106 (by detents, etc.), holding the second implant 104 in position on the needle 100 which is the initial position of the first implant 102.

FIG. 14 shows the delivery system moved to another location relative to the tissue 120 with a distal end of the delivery system (e.g., the distal end of the elongate shaft 118) positioned adjacent the tissue 120. FIG. 15 shows the needle 100 advanced through the tissue 120 on the other side of the tissue 120 with the distal tip of the needle 100 on the far side of the tissue 120 and the second implant 104 also on the far side of the tissue 120. The engaged tube 116 facilitates the advancement of the second implant 104 through the tissue 120 with the needle 100. The needle 100, the tube 116, and the second implant 104 have been advanced through the tissue 120 by moving the movable handle 106 distally toward and relative to the stationary handle 108. For clarity of illustration of the needle 100, second implant 104, and suture 122, the tube 116 is shown in FIG. 15 in a distal, non-advanced position instead of its actual, advanced position with a distal end thereof abutting a proximal end of the second implant 104.

FIG. 16 shows the needle 100 retracted from the far side of the tissue 120 to the near side of the tissue 120 with the second implant 104 remaining on the far side of the tissue 120 and with the suture 122 extending between the first and second implants 102, 104. The needle 100 has been retracted back through the tissue 120 by moving the movable handle 106 proximally away from and relative to the stationary handle 108. Other methods for inserting and deploying first and second implants include, for example, OmniSpan® and TrueSpan™ instrumentation available from DePuy Mitek of Raynham, Mass.

FIG. 17 shows the first and second implants 102, 104 having been toggled into position against the tissue 120 by tensioning the suture 122, e.g., by pulling the suture tail 122t to slide the suture 122 through the finger trap 124 and knot 126 and collapse an adjustable loop of the suture 122. The suture's finger trap 124 and knot 126 are located outside of the tissue 120 on the near side thereof in FIGS. 14-17 with the suture's tail 122t extending from the knot 126 so as to be accessible for use in tensioning, but the finger trap 124 and/or knot 126 may be partially or fully within the tissue 120 with the suture's tail 122t extending out of the tissue 120 before and after tensioning. The suture tail 122t can be trimmed after desired tensioning to allow removal of excess material from the patient's body. The tail 122t can be trimmed as close as possible to the knot 126 to reduce an amount of suture tail 122t remaining in the patient's body, which may minimize damage to the cartilage and/or other material adjacent thereto by rubbing thereagainst during post-surgery movement of the patient since the tail 122t will be minimally present, if present at all.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a first implantable anchor;
   a second implantable anchor; and
   a suture coupled to the first and second anchors, the suture having a first length extending from the first anchor toward the second anchor and having a second length extending from the second anchor toward the first anchor, the first length having a knot formed therein, wherein the knot is selected from the group consisting of an overhand knot, a hitch knot, a bend knot, a static knot, a sliding knot, and a collapsing knot, and the second length passing through a hollow portion formed in a body of the suture and then passing through the knot with a tail of the suture extending from the knot, the hollow portion being formed in the first length and being the only hollow portion in the body of the suture.

2. The device of claim 1, wherein the tail of the suture is configured to be pulled in a first direction toward the first anchor to tension the suture, and is configured to be pulled in a second, different direction to tension the suture.

3. The device of claim 2, wherein pulling the tail of the suture in the first direction is configured to reduce a distance between the first and second anchors, and pulling the tail of the suture in the second direction is configured to reduce the distance between the first and second anchors.

4. The device of claim 2, wherein pulling the tail of the suture in the first direction is configured to cause the suture to slide within the hollow portion and through the knot, and pulling the tail of the suture in the second direction is configured to cause the suture to slide within the hollow portion and through the knot.

5. The device of claim 2, wherein the suture is slidable through the hollow portion in only the first direction.

6. The device of claim 1, wherein the second length exits the hollow portion before passing through the knot.

7. The device of claim 1, wherein the first anchor has a first hole through which the suture extends, and the second anchor has a second hole through which the suture extends.

8. The device of claim 1, further comprising a second suture coupled to the second anchor and having the suture looped therethrough so as to couple the suture to the second anchor.

9. The device of claim 1, wherein the suture is braided from a plurality of threads.

10. A surgical device, comprising:
    a first implantable anchor;
    a second implantable anchor;
    a first suture attached to the first anchor, the first suture including a hollow portion through which another portion of the first suture passes through, a knot being adjacent to the hollow portion such that a tail of the first suture passes through the hollow portion and then passes through the knot, the tail being configured to be pulled to slide the first suture through the hollow portion and through the knot; wherein the knot is selected from a group consisting of an overhand knot, a hitch knot, a bend knot, a static knot, a sliding knot, and a collapsing knot; and
    a second suture attached to the second anchor, the second suture defining a loop through which the first suture passes.

11. The device of claim 10, wherein the tail is configured to be pulled in any direction to slide the first suture through the hollow portion and through the knot.

12. The device of claim 10, wherein the hollow portion and the knot are located along a length of first suture extending between the first and second anchors.

13. The device of claim 10, wherein pulling the tail to slide the first suture through the hollow portion and through the knot reduces a distance between the first and second anchors.

14. The device of claim 10, wherein the first suture defines an adjustable loop, the adjustable loop passes through the loop defined by the second suture, and pulling the tail to slide the first suture through the hollow portion and through the knot collapses the adjustable loop.

15. A surgical method, comprising:
    advancing a suture, a first anchor, and a second anchor into a body of a patient with the suture extending between the first and second anchors, having a knot formed therein, wherein the knot is selected from a group consisting of an overhand knot, a hitch knot, a bend knot, a static knot, a sliding knot, and a collapsing knot, and having a hollow portion adjacent the knot through which another portion of the suture extends; and advancing each of the first and second anchors through a soft tissue and then, with the suture extending through the tissue and between the first and second anchors, tensioning the suture to cause the suture to slide through the knot and through the hollow portion and cause the first and second anchors to move relative to the tissue.

16. The method of claim 15, wherein the suture is uni-directionally slidable through the hollow portion in a first direction, and tensioning the suture includes pulling a tail of the suture extending from the knot in the first direction.

17. The method of claim 15, wherein the suture is uni-directionally slidable through the hollow portion in a first direction, and tensioning the suture includes pulling a tail of the suture extending from the knot in a second, different direction.

18. The method of claim 15, wherein the tissue is at one of a knee, a hip, and a shoulder of the patient.

\* \* \* \* \*